(12) United States Patent
Ahlmen et al.

(10) Patent No.: US 6,878,133 B2
(45) Date of Patent: Apr. 12, 2005

(54) DELIVERY APPARATUS FOR PRESSURIZED MEDICAL LIQUIDS

(75) Inventors: Christer Ahlmen, Sollentuna (SE); Petter Videbrink, Upplands Vasby (SE)

(73) Assignee: Maquet Critical Care AB, Solna (SE)

( * ) Notice: Subject to any disclaimer, the term of this patent is extended or adjusted under 35 U.S.C. 154(b) by 34 days.

(21) Appl. No.: 10/238,568

(22) Filed: Sep. 10, 2002

(65) Prior Publication Data

US 2003/0066845 A1 Apr. 10, 2003

(30) Foreign Application Priority Data

Oct. 4, 2001 (SE) .............................................. 0103311

(51) Int. Cl.⁷ .......................... A61M 37/00; A61M 5/00
(52) U.S. Cl. ...................................... 604/132; 604/246
(58) Field of Search ........................ 604/288.04, 93.01, 604/131, 132, 133, 134, 135, 140, 141, 143, 146, 147, 151, 152, 207, 209, 212, 213, 214, 215, 218, 246, 248, 257, 288.01, 288.02, 288.03, 208

(56) References Cited

U.S. PATENT DOCUMENTS 4,221,219 A * 9/1980 Tucker ........................ 604/141
4,613,060 A 9/1986 Ulbrich et al.
4,684,367 A * 8/1987 Schaffer et al. .............. 604/140
4,825,860 A 5/1989 Falb et al.
5,235,971 A 8/1993 Falb et al.
5,645,052 A 7/1997 Kersey
5,904,188 A 5/1999 Heinonen et al.

FOREIGN PATENT DOCUMENTS

| DE | 41 16 512 | 11/1992 |
| DE | 101 53 043 | 10/2002 |
| EP | 0 781 571 | 7/1997 |
| GB | 964414 | 7/1964 |
| WO | WO 92/12752 | 8/1992 |

* cited by examiner

Primary Examiner—Nicholas D. Lucchesi
Assistant Examiner—Mark K. Han
(74) Attorney, Agent, or Firm—Schiff Hardin LLP

(57) ABSTRACT

A delivery apparatus for pressurized medical liquids has a primary reservoir and a primary pressurizing arrangement configured for removably pressurizing medical liquid in the primary reservoir to a delivery pressure. A secondary reservoir has an inlet connected via a valve to receive pressurized liquid from the primary reservoir. As secondary pressurizing arrangement is arranged for supplying a compensating pressure to the received pressurized liquid to maintain it at substantially the delivery pressure as pressure is reduced in the primary reservoir, particularly during refilling with medical liquid from an unpressurized source.

7 Claims, 5 Drawing Sheets

DELIVERY APPARATUS FOR PRESSURIZED MEDICAL LIQUIDS

BACKGROUND OF THE INVENTION

1. Field of the Invention

The present invention relates to a delivery apparatus for pressurized medical liquids and in particular to a re-fillable delivery apparatus for pressurized liquid anaesthetics.

2. Description of the Prior Art

It is known to provide a delivery apparatus for pressurized liquid anaesthetic which has a primary reservoir having an inlet for refilling with the liquid anaesthetic, a primary pressurizing arrangement, typically a source of pressurized inert gas and a pressure regulator, for maintaining liquid within the primary reservoir at a delivery pressure, and an outlet through which the pressurized liquid anaesthetic is controllably delivered at the delivery pressure. Normally, to refill the primary reservoir of this known apparatus either the delivery pressure must be removed and fresh liquid introduced through the inlet at atmospheric pressure, or liquid anaesthetic at the delivery pressure must be introduced through the inlet. The former has the disadvantage that the delivery of the pressurized liquid anaesthetic must be stopped during refilling and the latter has the disadvantages that pressurized liquid anaesthetic may escape into the local environment or that the delivery apparatus may become over-pressurized, which may cause either escape of anaesthetic into the local environment or an error in the delivered amount of the liquid anaesthetic.

SUMMARY OF THE INVENTION

It is an object of the present invention to provide a delivery apparatus for pressurized medical liquids which avoids the aforementioned disadvantages of known delivery systems of this type.

This object is achieved in accordance with the principles of the present invention in a delivery apparatus having a primary reservoir for a medical liquid and a primary pressurizing arrangement for pressurizing the medical liquid in the primary reservoir to a delivery pressure, a secondary reservoir having an inlet connected to receive the pressurized medical liquid from the primary reservoir, an outlet for discharging the received pressurized liquid, and a secondary pressurizing arrangement for supplying a compensating pressure to the received pressurized liquid in the secondary reservoir, to maintain the received pressurized liquid at substantially the delivery pressure, as pressure is reduced within the primary reservoir.

By providing a secondary reservoir having an associated secondary pressurizing arrangement configured to maintain the liquid in the secondary reservoir at or close to the desired delivery pressure, a reduction in applied pressure in the primary reservoir can then be compensated for, which advantageously permits continued operation of the apparatus even in the absence or reduction of delivery pressure from the primary pressurizing arrangement. This has an advantage that the primary reservoir may be refilled at or about atmospheric pressure without interruption of delivery of the pressurized liquid.

The secondary pressurizing arrangement may be formed simply by a moveable section, such as a membrane, arranged to be moved by the application of a bias force, such as may be supplied from a mechanical biasing element or from the pressurizing gas source, to reduce the volume of the liquid containing portion of the secondary reservoir as the volume of liquid is reduced, primarily by exit through the outlet.

The movable section may be provided with a sealing head which is pressed against the outlet to form a liquid tight seal as the volume of liquid within the secondary reservoir reaches a predetermined minimum. The sealing head thus may act as a safety valve, stopping delivery when the amount of suitably pressurized liquid within the secondary reservoir falls to a predetermined, even zero, level.

A valve arrangement, such as a one-way or on/off valve arrangement, for controlling flow of liquid from the secondary reservoir into the primary reservoir may be connected to the inlet of the secondary reservoir. This controls flow back into the primary reservoir as the delivery pressure is removed from liquid therein and may be configured to enable substantially all of the liquid within the secondary reservoir to be made available for delivery through the outlet, which is particularly advantageous during refilling of the primary reservoir.

DESCRIPTION OF THE PREFERRED EMBODIMENTS

Figure 1A:
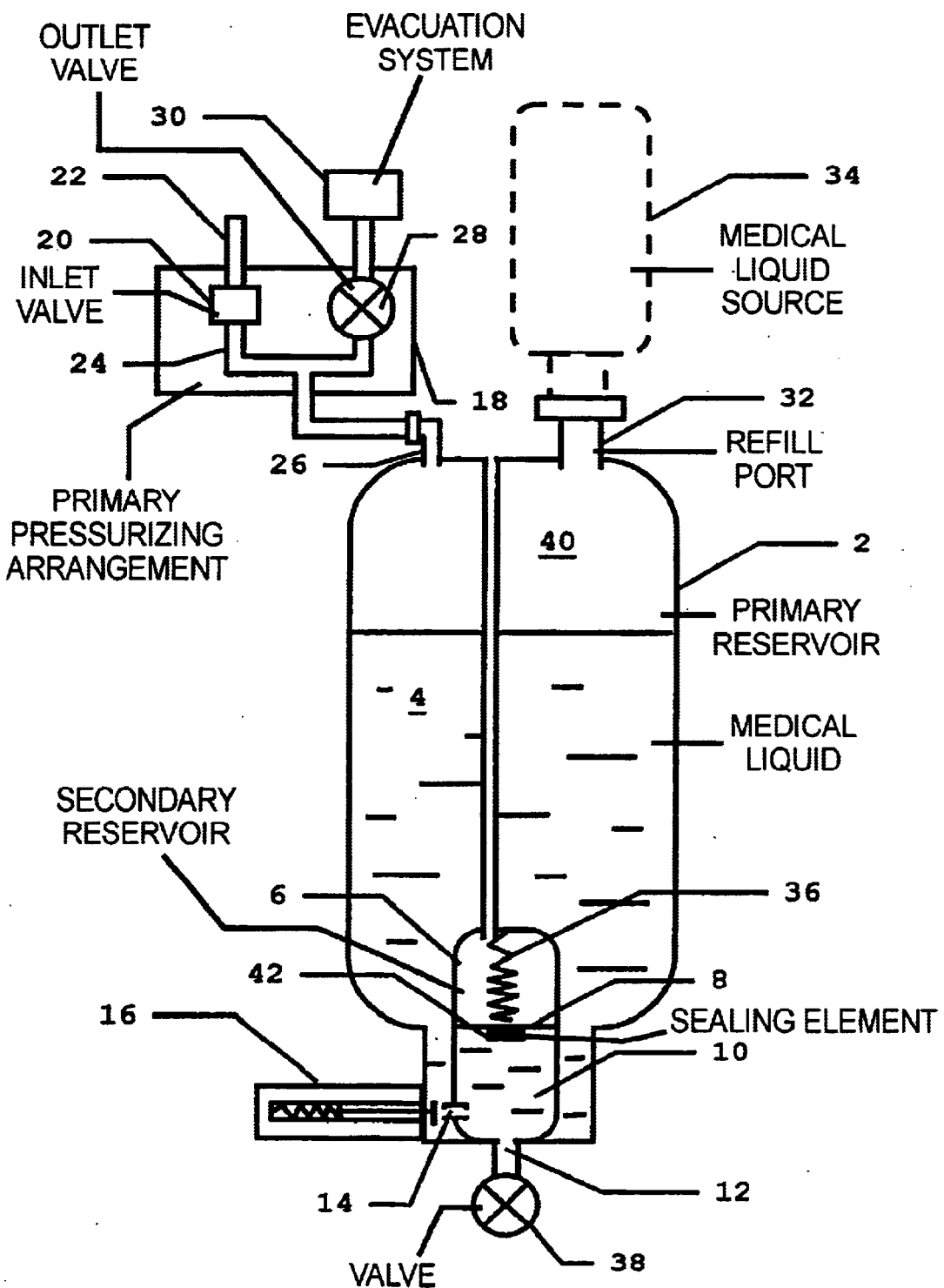
FIGS. 1a, 1b and 1c illustrate a first embodiment of a delivery apparatus according to the present invention.
Figure 1B:
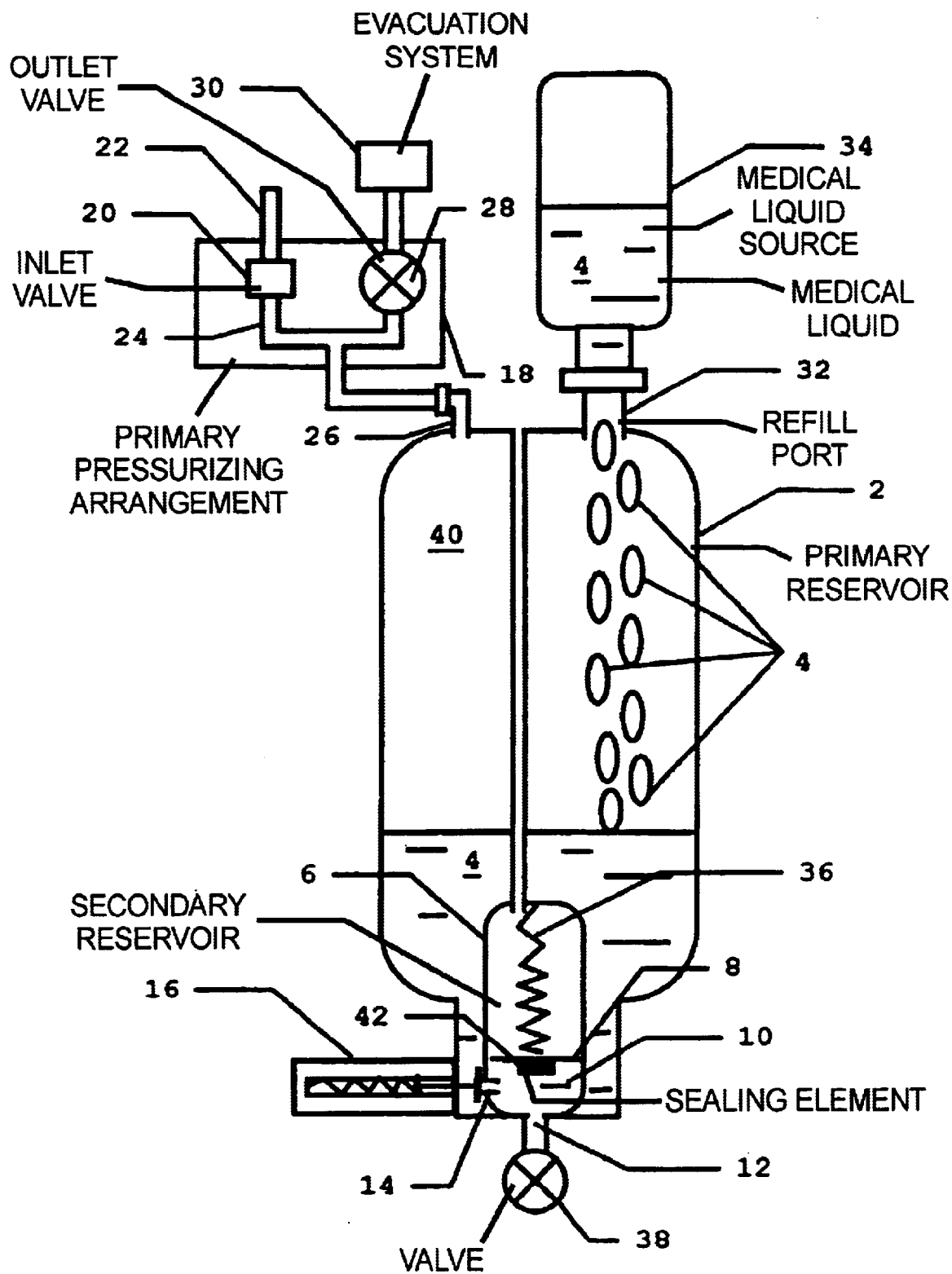
Figure 1C:
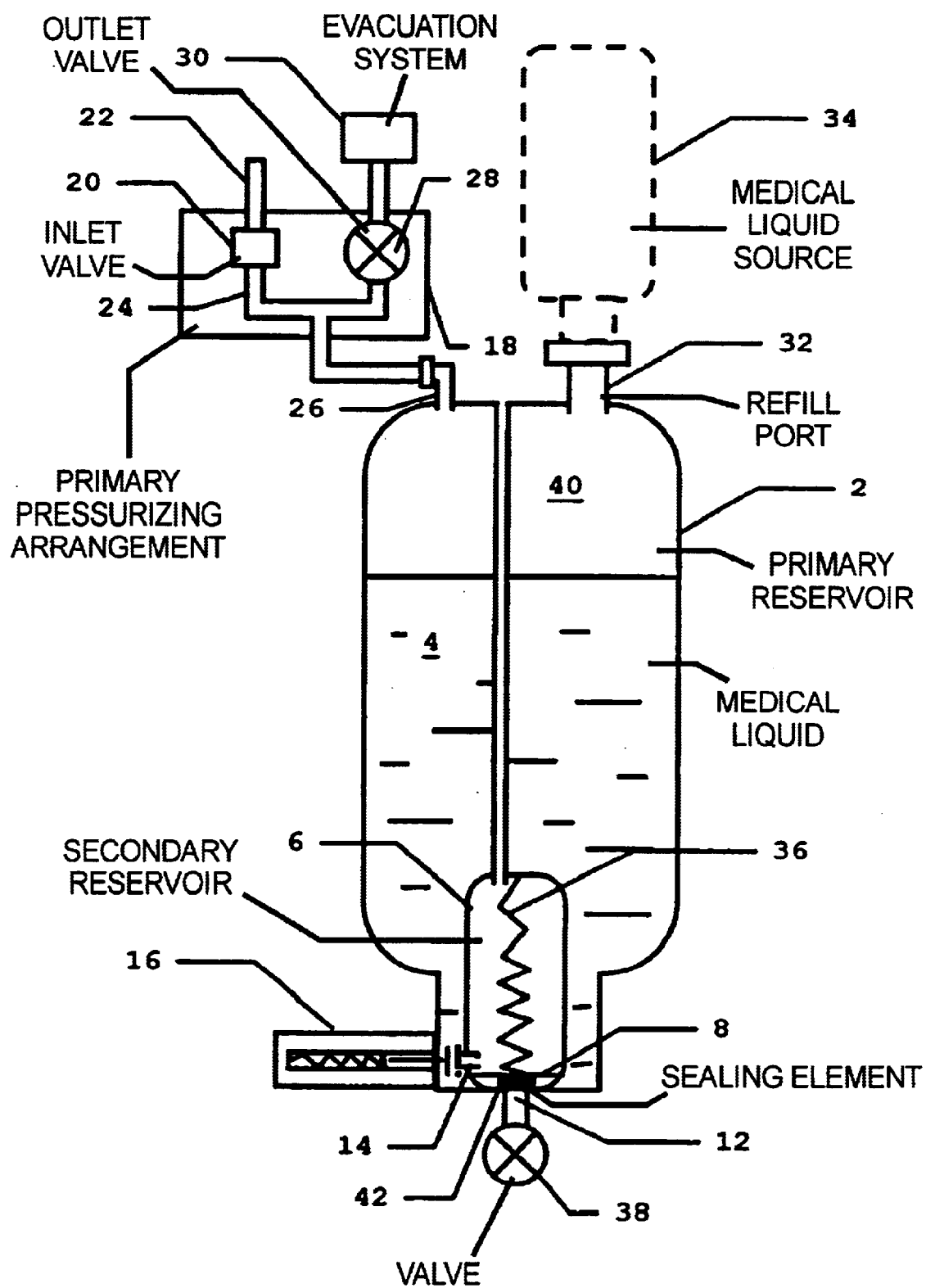

In FIGS. 1a, 1b and 1c, a delivery apparatus is shown having an outer, primary reservoir 2 for medical liquid 4 and an inner, secondary reservoir 6 which is arranged within the primary reservoir 2. The secondary reservoir 6 is provided with a movable membrane 8 which delimits an inner variable volume liquid containing space 10. The space 10 is connected for fluid communication to an outlet 12 from the apparatus. An inlet 14 is provided in a wall of the secondary reservoir 6 and provides a liquid passage for liquid to flow from primary reservoir 2 into the variable volume space 10. A valve 16 is in communication with the inlet 14 and is operable to seal it against the flow-through of medical liquid. Although shown in the present embodiment as an on/off valve, it will be appreciated by those skilled in the art from a consideration of this description that the valve 16 may be a one-way valve or any other valve which operates to prevent the flow of pressurized liquid from the secondary reservoir 6 back to the primary reservoir 2.

A primary pressurizing arrangement 18 is connected to the primary reservoir 2 and has a pressure regulating inlet valve 20 with an inlet side 22 for connection to a source of pressurized gas (not shown) and an outlet side 24 connected to a gas port 26 through which pressurized gas may flow into and out of the primary reservoir 2. Also connected to the gas port 26 is an outlet valve 28 through which gas from within the primary reservoir 2 may pass to either the atmosphere or, as shown, to an evacuation system 30 which either actively or passively recovers gas.

A resealable refill port 32 is provided for the transfer of medical liquid from a source 34 connectable to the port 32 and into the primary reservoir 2.

A secondary pressurizing arrangement has a bias element, here a spring bias 36 but which may be pneumatic or electromechanical, cooperably arranged with the membrane 8 to tend to move the membrane 8 so as to reduce the volume of the variable volume space 10.

FIG. 1a shows the above described delivery apparatus configured for the delivery of pressurized medical liquid through the outlet 12 in amounts controlled by the opening and closing of an external valve 38 to which the outlet 12 is connectable. The pressure regulation valve 20 of the primary pressurization arrangement 18 controls the flow of pressurized gas from the source of pressurized gas to maintain a pressure head of gas in a space 40 in the primary reservoir 2 above the medical liquid 4 sufficient to pressurize the liquid 4 to a desired delivery pressure. The valve 16 is open and pressurized liquid from the primary reservoir 2 flows into the variable volume space 10, forcing the membrane 8 to move against the bias element 32 and increase the volume of the space 10 until the force exerted on the membrane 8 by the bias element 32 balances that exerted on the membrane by the pressurized fluid. At this point the secondary reservoir 2 is filled with medical liquid at the delivery pressure generated by the primary pressurizing arrangement 18. If the pressure of gas in the space 40 above the medical liquid 4 in the primary reservoir 2 varies then this may be compensated for by changes in location of the membrane 8 so as to maintain the liquid within the variable volume space 10 of the secondary reservoir 2 at substantially that of the desired delivery pressure. In particular this permits the operation of the apparatus to continue delivery of suitably pressurized liquid through the outlet 12 even when the primary reservoir 2 is being refilled from the source of medical liquid 32 at or close to atmospheric pressure, as illustrated in FIG. 1b.

Considering now FIG. 1b, during refilling of the present embodiment the primary pressurising means 18 operates to remove the delivery pressure by closing the valve 20 and opening the outlet valve 28. Simultaneously with, or preferably before this occurs, the inlet 14 to the secondary reservoir 6 is closed by the valve 16. The source of medical liquid 34 is connected to the refill port 32 which is opened to refill the reservoir 2 with medical liquid from the unpressurized source 34. The outlet valve 28 may be closed during refilling to prevent loss of medical agent from the apparatus. This is particularly useful if the evacuation system 30 operates to actively (suction) recover gas or if the medical liquid volatilizes readily.

Once the reservoir 2 is refilled the port 32 is closed and the pressurizing arrangement operated to re-establish the delivery pressure. The valve 16 is then operated to open the inlet 14 to allow pressurized liquid from the primary reservoir 2 to enter the variable volume space 10 of the secondary reservoir, returning the apparatus to the operating condition illustrated in FIG. 1a.

As shown in FIG. 1b, during the refill procedure pressurized liquid at substantially the delivery pressure continues to be delivered through the outlet 12, under the control of the valve 38. As liquid leaves the secondary reservoir 6 the biasing element 36 applies a force to the movable membrane 8 sufficient to reduce the volume of the variable volume space 10 so as to maintain the remaining liquid at substantially the delivery pressure.

The membrane 8 also is provided with a sealing element 42 which moves with the membrane 8 and can be urged against the outlet 12 by the biasing element 36 as the membrane 8 is moved to reduce the volume of the space 10 to a minimum. This stops delivery of the medical liquid from the secondary reservoir 6 and can be operated to act as a safety valve. This operating position is shown in FIG. 1c for a circumstance in which the pressure in the space 40 is reduced from the delivery pressure. The valve 16 is operated to open the inlet 14. Pressurized liquid within the space 10 flows back into the primary reservoir 2 and the sealing surface 42 is moved to seal the outlet 12 and prevents further transfer of medical liquid 4 from the delivery apparatus. The valve 16 may then be operated to close (dashed position) the inlet 14 of the secondary reservoir 6 and thus acts as a secondary safety valve.

Figure 2A:
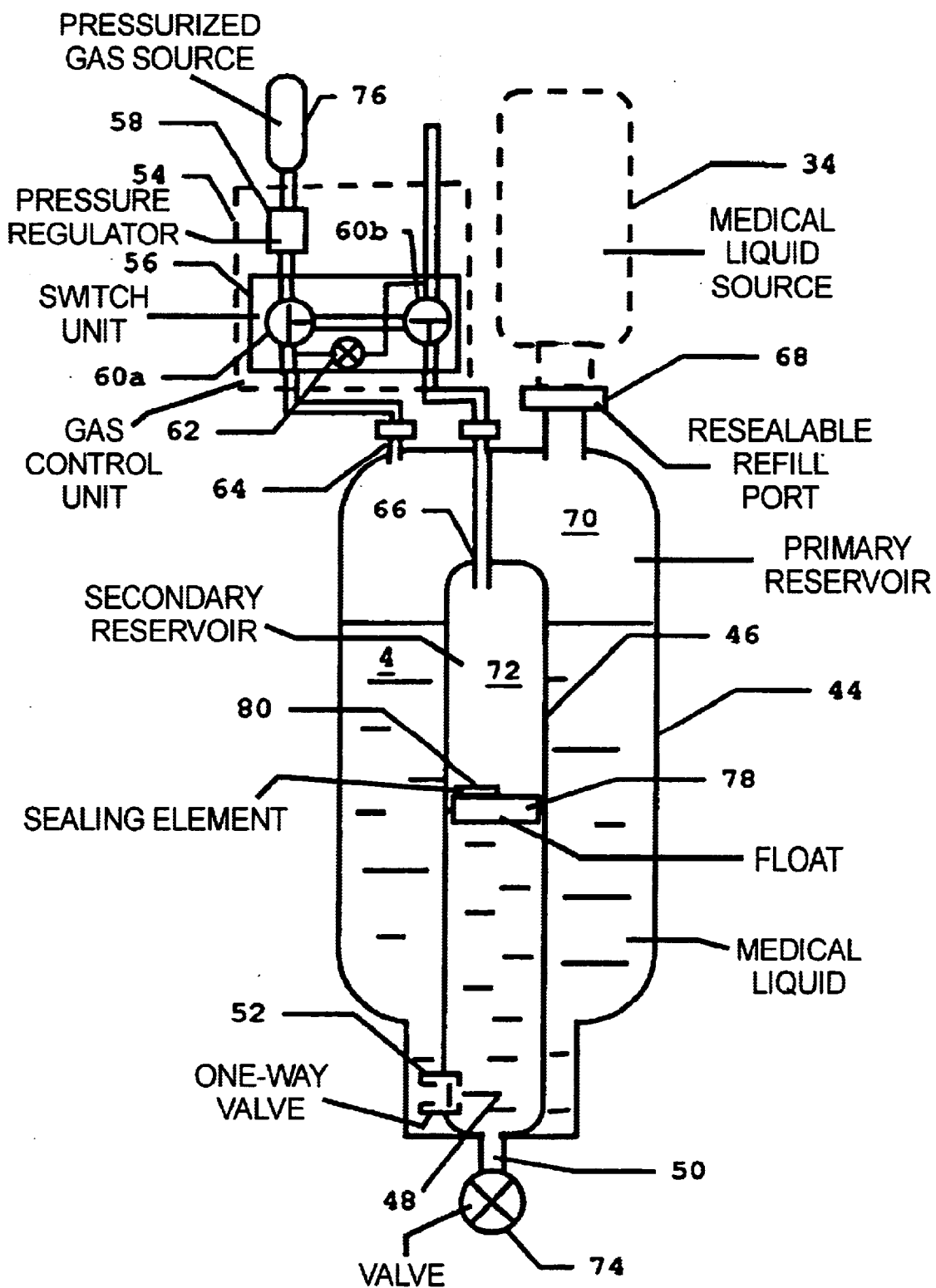
FIGS. 2a and 2b illustrate a second embodiment of a delivery system according to the present invention.
Figure 2B:
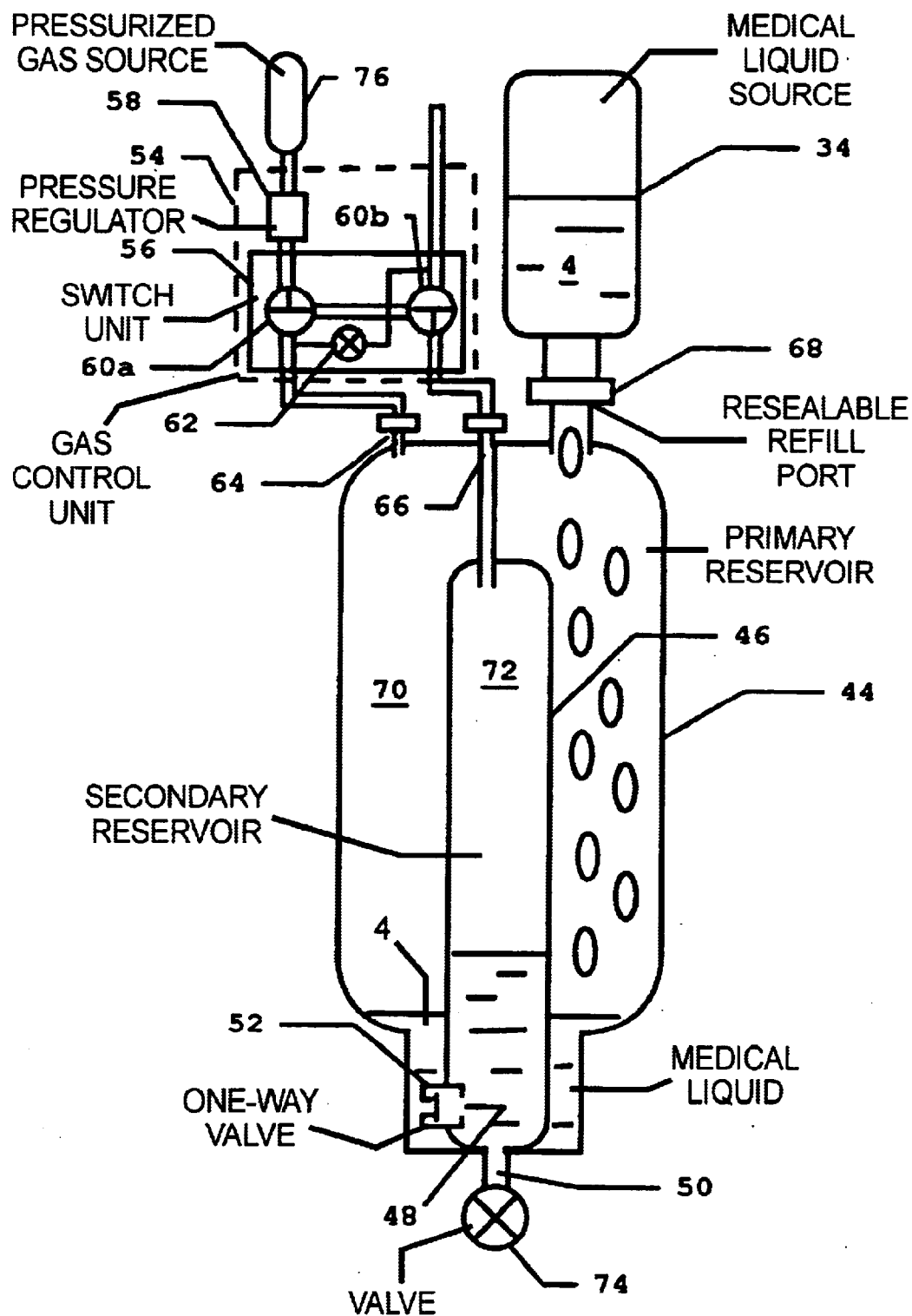

Considering now the embodiment shown in FIGS. 2a and 2b a delivery apparatus is shown comprising an outer, primary reservoir 44 for medical liquid 4 and an inner, secondary reservoir 46 which is arranged within the primary reservoir 44. An inlet 48 is provided in a wall of the secondary reservoir 46 and provides a passage for liquid to flow from primary reservoir 44 into the secondary reservoir 46 from where it can leave the apparatus through an outlet 50. A one-way valve 52 is in communication with the inlet 48 and is operable to seal it against the flow-through of medical liquid from the secondary reservoir 46 back into the primary reservoir 44.

A gas control unit 54 has a switch unit 56 having a number of flow path selectors (such as 'T' valves 60a, 60b) and on/off valves (for example 62) which can be operated to selectively connect a gas flow from a source of pressurized gas 76 via a pressure regulator 58 to one or both gas ports 64, 66 of the primary 44 and secondary 46 reservoirs, respectively. The valves 60a, 60b and 62 are arranged such that one or both of the gas ports 64, 66 can be connected to atmosphere. Thus by selective operation of the switch unit 56 the valves 60a, 60b and 62 can be positioned so that the pressurized gas from the regulator 58 can be introduced into one or both spaces 70, 72 above liquid in the primary 44 and secondary 46 reservoirs respectively to pressurize the liquid 4 contained in the reservoirs 44,46 to a predetermined delivery pressure.

A re-sealable refill port 68 is provided for the transfer of medical liquid from a source 34 connectable to the port 32 and into the primary reservoir 44.

FIG. 2a shows the above described delivery apparatus configured for the delivery of pressurized medical liquid through the outlet 50 in amounts controlled by the opening and closing of an external valve 74 to which the outlet 50 is connectable. The switch unit 56 causes the valves 60a,b, and 62 to operate to allow the spaces 70,72 to receive pressurized gas and thus the medical liquid 4 in the primary reservoir 44 to be pressurized to the desired delivery pressure. Pressurized liquid may then move from the primary reservoir 44, via the secondary reservoir 46 to the outlet 50 from where pressurized medical liquid may be delivered externally of the apparatus under the control of the valve 74.

Optionally, and as illustrated in FIG. 2a a float 78 may be provided in the secondary reservoir 46 and is provided with a sealing element 80. This element 80 is disposed on the float 78 so as to be capable of sealing the gas port 66 as the level of liquid 4 within the secondary reservoir 46 rises to urge the float against the open end 82. The float arrangement 78,80 is useful in that it effectively prevents escape of liquid through the gas port 66 in the event of the accidental connection of the gas port 66 to atmosphere while the primary reservoir 44 remains pressurized.

FIG. 2b illustrates re-filling of the primary reservoir 44 from the source of unpressurized medical liquid 34 which is connected to the sealed refill port 68. The valve 62 is opened to connect the space 70 of the primary reservoir to atmosphere and the flow path selectors 60a, 60b are moved to connect the pressure regulator only to the space 72 above the medical liquid 4 in the secondary reservoir. Flow of liquid 4 from the secondary reservoir 46 into the primary reservoir 44 is prevented by the one-way valve 52. The pressure in the primary reservoir 44 is thus reduced to atmospheric whilst the liquid 4 within the secondary reservoir 46 remains substantially at the delivery pressure.

The refill port 68 may then be unsealed and medical liquid 4 can flow from the source 34. Any pressure decrease in the space 72 as the level of pressurized fluid in the secondary reservoir 46 decreases is compensated for by supply of additional pressurized gas via the pressure regulator 58.

It will be appreciated from the above description that the delivery apparatus of FIGS. 2*a* and 2*b* is able to maintain a delivery of medical liquid substantially at the delivery pressure whilst refilling at atmospheric pressure is underway.

Although modifications and changes may be suggested by those skilled in the art, it is the intention of the inventors to embody within the patent warranted hereon all changes and modifications as reasonably and properly come within the scope of their contribution to the art.

We claim as our invention:

1. A delivery apparatus for a medical liquid, comprising:
    a primary reservoir containing a medical liquid;
    a primary pressurizing arrangement in communication with said primary reservoir for pressurizing said medical liquid therein to a delivery pressure produced by said primary pressurizing arrangement;
    a secondary reservoir having an inlet connected to receive said medical liquid from said primary reservoir, as received pressurized liquid, and having an outlet allowing discharge of said pressurized liquid at said delivery pressure; and
    a secondary pressurizing arrangement for interacting with said pressurized liquid in said secondary reservoir to maintain said received pressurized liquid substantially at said delivery pressure independently of whether said medical liquid in said primary reservoir is maintained at said delivery pressure.

2. A delivery apparatus as claimed in claim 1 wherein said secondary reservoir has a liquid holding space with a variable volume, and wherein said secondary pressurizing arrangement varies said volume of said liquid holding space to maintain said received pressurized liquid substantially at said delivery pressure.

3. A delivery apparatus as claimed as claim in claim 2 wherein said secondary reservoir has a movable wall section delimiting at least a portion of said variable volume space, and a biasing element disposed to bias said movable wall section in a direction for reducing said volume of said liquid holding space as said received pressurized liquid is discharged through said outlet.

4. A delivery apparatus as claimed in claim 3 wherein said movable wall section is movable in said secondary reservoir to a movement limit location defining a minimum volume of said received pressurized liquid in said secondary reservoir, and wherein said movable wall section has a sealing element disposed to seal against said outlet when said movable wall section is at said movement limit location.

5. A delivery apparatus as claimed in claim 1 wherein said secondary reservoir has a gas holding space, disposed above said received pressurized liquid in said secondary reservoir, and has an access port for connecting said gas holding space to a source of pressurized gas for generating a pressure head in said gas holding space above said received pressurized liquid to maintain said received pressurized liquid in said secondary reservoir substantially at said delivery pressure.

6. A delivery apparatus as claimed in claim 5 further comprising a float disposed in said secondary reservoir, adapted to float in said received pressurized liquid in said secondary reservoir, and having a sealing element disposed to seal against said access port when a level of said received pressurized liquid in said secondary reservoir reaches a predetermined level.

7. A delivery apparatus as claimed in claim 1 further comprising a valve arrangement interacting with said inlet of said secondary reservoir to inhibit back flow of said received pressurized liquid from said secondary reservoir into said primary reservoir.

* * * * *